US007372051B2

(12) United States Patent
Tsuneta et al.

(10) Patent No.: US 7,372,051 B2
(45) Date of Patent: May 13, 2008

(54) ELECTRIC CHARGED PARTICLE BEAM MICROSCOPY, ELECTRIC CHARGED PARTICLE BEAM MICROSCOPE, CRITICAL DIMENSION MEASUREMENT AND CRITICAL DIMENSION MEASUREMENT SYSTEM

(75) Inventors: Ruriko Tsuneta, Fucha (JP); Hiromi Inada, Hitachinaka (JP); Masanari Koguchi, Kunitachi (JP); Takahito Hashimoto, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 330 days.

(21) Appl. No.: 11/189,897

(22) Filed: Jul. 27, 2005

(65) Prior Publication Data

US 2006/0038125 A1 Feb. 23, 2006

(30) Foreign Application Priority Data

Aug. 23, 2004 (JP) .............................. 2004-242103

(51) Int. Cl.
*G21K 7/00* (2006.01)
*H01J 37/26* (2006.01)
(52) U.S. Cl. .................... 250/492.3; 250/306; 250/307; 250/310; 250/311; 250/397
(58) Field of Classification Search ................. 250/306, 250/492.3
See application file for complete search history.

(56) References Cited

U.S. PATENT DOCUMENTS 4,818,873 A * 4/1989 Herriot ........................ 250/310
4,835,402 A * 5/1989 Guillaume ............. 250/559.22
4,871,912 A * 10/1989 Kokubo et al. ............. 250/311
5,424,853 A * 6/1995 Miyaza ........................ 358/451
5,517,326 A * 5/1996 Miyaza et al. .............. 358/450
5,532,494 A * 7/1996 Kawanami et al. ...... 250/491.1
5,589,949 A * 12/1996 Miyaza et al. .............. 358/451
5,663,809 A * 9/1997 Miyaza et al. .............. 358/450
5,671,463 A * 9/1997 Morikawa et al. ............ 399/86
5,750,990 A * 5/1998 Mizuno et al. ............. 250/307
5,834,774 A * 11/1998 Negishi et al. ............. 250/310
6,815,677 B2 * 11/2004 Nagai et al. ................ 250/310

(Continued)

FOREIGN PATENT DOCUMENTS

JP      2000-337846     12/2000

(Continued)

*Primary Examiner*—David A. Vanore
*Assistant Examiner*—Bernard Souw
(74) *Attorney, Agent, or Firm*—Antonelli, Terry, Stout & Kraus, LLP.

(57) ABSTRACT

Magnification errors are reduced in the required range of magnification in electric charged particle beam application apparatuses and critical dimension measurement instruments. To achieve this, a first image, whose magnification for the specimen is actually measured, is recorded, a second image, whose magnification for the specimen is unknown, is recorded, and the magnification of the second image for the first image is analyzed by using image analysis. Thereby, the magnification of the second image for the specimen is actually measured. Then, magnification is actually measured in the whole range of magnification by repeating the magnification analysis described above by taking the second image as the first image. Actually measuring the magnification of images for the specimen in the whole range of magnification and calibrating the same permits a reduction of magnification errors by a digit.

10 Claims, 11 Drawing Sheets

U.S. PATENT DOCUMENTS

| | | | |
|---|---|---|---|
| 6,861,181 B1 * | 3/2005 | Henderson | 430/5 |
| 6,867,606 B2 * | 3/2005 | Pinto et al. | 324/751 |
| 6,868,175 B1 * | 3/2005 | Yamamoto et al. | 382/145 |
| 6,873,747 B2 * | 3/2005 | Askary | 382/295 |
| 6,890,505 B2 * | 5/2005 | Miyazawa et al. | 423/447.2 |
| 6,961,457 B2 * | 11/2005 | Sugawara | 382/151 |
| 2006/0038125 A1 * | 2/2006 | Tsuneta et al. | 250/310 |
| 2006/0192574 A1 * | 8/2006 | Furukawa et al. | 324/750 |

FOREIGN PATENT DOCUMENTS

JP     2002-15691     1/2002

* cited by examiner

ELECTRIC CHARGED PARTICLE BEAM MICROSCOPY, ELECTRIC CHARGED PARTICLE BEAM MICROSCOPE, CRITICAL DIMENSION MEASUREMENT AND CRITICAL DIMENSION MEASUREMENT SYSTEM

CLAIM OF PRIORITY

The present application claims priority from Japanese application JP 2004-242103, filed on Aug. 23, 2004, the content of which is hereby incorporated by reference into this application.

FIELD OF THE INVENTION

The present invention relates to an electric charged particle beam system for measuring the critical dimension of specimens, and to a critical dimension measurement system used in the examination and analysis of patterns in semiconductor devices.

BACKGROUND OF THE INVENTION

As an apparatus which may be used for measuring the critical dimension of specimens to a precision in the order of a nanometer, there is, for example, an electron microscope. An electron microscope forms an image of a specimen by enlarging it from several hundreds of times to several millions of times, and it measures the critical dimension of necessary parts. However, the critical dimension measured in the enlarged image is the number of picture elements or pixels contained therein. The critical dimension of a specimen is calculated by multiplying the number of pixels by the magnification of the image for the specimen. The question of whether the critical dimension of the specimen is a real value or not depends on whether the magnification is a real value or not.

As an apparatus that is capable of determining the precision of measurement of the critical dimension of specimens, there is a SEM (scanning electron microscope) for critical dimension measurement. The SEM for critical dimension measurement is now considered to be an apparatus that is indispensable for pattern dimension management in the fabrication process used in the manufacture of semiconductor devices. Because of the necessity for critical dimension measurements to correspond with real values in an SEM for critical dimension measurement, the magnification is calibrated with a pitch pattern having a known cycle of repetition. Patent Document 1 (Japanese Patent Laid Open Publication No. 2002-15691) describes a technique for measuring variations in magnification when the acceleration voltage and the working distance (distance between objective lens and specimen) have changed by using standard specimen, such as a mesh, and of calibrating the displayed magnification and a scale bar. Patent Document 2 (Japanese Patent Laid Open Publication No. 2000-337846) describes a technique for measuring variations in magnification resulting from an increase in the acceleration voltage, from the retarding voltage and from the specimen by using a pitch pattern having a known cycle of repetition and of calibrating the magnification by multiplying the sit magnification by a calibration coefficient.

The magnification range of an electron microscope extends from manufactures of several hundreds of times to several millions of times. However, the magnification range in which a calibration is possible by using a standard specimen is very limited. Specifically, the cycle of a pitch pattern realizable by the present processing art is several hundreds of nm. In order to average the processing errors, images containing 10 or more pitch patterns are taken. The cycle (number of pixels) of pitch patterns shown in the image is acquired from the Fourier transform image of the image, which calculates the magnification that turns out to be the cycle (nm) of the pitch patterns. The magnification at which an image contains approximately 10 pitch patterns is approximately 10,000 times. The patent publication mentioned above describes the calibration of magnification based on use of an SEM. However, electron microscopes include TEM (transmission electron microscope) and STEM (scanning transmission electron microscope) types in addition to the SEM type. The SEM visualizes the specimen structure by detecting an electron beam radiating from the specimen surface, while the TEM and STEM visualize the specimen structure by detecting an electron beam that has infiltrated into the specimen. For that purpose, the TEM and STEM slice the specimen into thin films for observation. Because of a limited dispersion of the electron beam within the specimen in the TEM and STEM, the space resolution of the TEM and STEM is higher by a digit than the resolution of the SEM. With the TEM and STEM, it is possible to take a lattice image, which is used together with the pitch pattern for the calibration of magnification. The lattice interval varies between the narrower limit of 0.102 nm for a gold single crystal and the wider limit of 1.0 nm for a mica single crystal. The magnification at which a lattice image can be observed is several millions of times or more. In other words, magnification calibration is possible by using specimens having a known cycle of repetition only when the magnification is 10,000 times or less or a million times or more.

Since a magnification cannot be calibrated by using a standard specimen between 10,000 times and a million times, a calculated value estimated from the control current of the electron optical system is typically used as a measure of the magnification of the image of the specimen. Specifically, in an apparatus like a SEM or STEM, wherein an image is formed by raster scanning a sharply focused electron beam on the specimen, the range of scanning or magnification of any freely chosen image is calculated on the basis of the current amplitude of the scanning deflector by assuming that the range of current of the scanning deflector and the scanning range of the incident electron beam are parallel. In an apparatus like a TEM wherein parallel beams are amplified by an electron lens, the magnification of any freely chosen image of the specimen is calculated by acquiring the optical magnification of the electron lens from the excitation current of the electron lens.

As described above, magnification is analyzed and calibrated from images actually taken only at very limited magnifications. At other magnifications, the magnification contains an error of approximately ±5% because of the use of magnifications calculated from the control current of the electron optical system. As nanotechnology continues to progress, a large number of industrial products formed in the nanometer scale are now being produced in addition to semiconductor devices. These products have a variety of dimensions, and the management of their dimensions is required at a variety of magnifications. As the device dimension decrease in semiconductor devices, it has become necessary to measure a pattern dimension at a magnification that is different from the magnification used for taking a pitch pattern.

SUMMARY OF THE INVENTION

The present invention addresses the afore-mentioned disadvantages by reducing magnification errors in a specified magnification range in an electric charged particle beam application system, critical dimension measurement system and the like.

The above-mentioned and other objects and novel features of the present invention will be clarified by the following description and the attached.

The present invention is preferably configured such that the magnification of a second image for the specimen is measured by recording the first image of which the magnification for the specimen has been measured, the second image of which the magnification for the specimen is unknown and by analyzing the magnification of the second image for the first image by using image analysis; and then, magnification can be measured from an image actually taken in the whole magnification range of the electron microscope by replacing the second image by the first image and by repeating the magnification analysis described above. According to the present invention, the precision of magnification setting of the electron microscope can be improved by a digit by recording the magnification actually measured together with the control condition of the electron microscope and by calibrating the magnification.

A first aspect of the present invention is directed to electric charged particle beam microscopy wherein specimens are irradiated with charged particle beams and secondary charged particle beams generated by the specimens are detected in order to obtain an image of the specimens. The electric charged particle beam microscopy preferably includes: a step of taking a first image with a known magnification to specimens by irradiating specimens with charged particle beams under a first control condition; a step of taking a second image having a common field of view with the first image by irradiating specimens with charged particle beams under a second control condition; a step of processing images for analyzing a magnification of the second image relative to the first image from the common field of view; a step of calculating the magnification of the second image to the specimen from the magnification of the first image to the specimen and the magnification of the second image to the first image; and a step of recording the magnification of the second image to the specimen along with the second control condition.

In the first aspect, it is preferable that the electric charged particle beam microscopy further includes: when the magnification of the second image relative to the first image cannot be analyzed in the step of image processing, a step of taking a third image having a common field of view with the first image by irradiating specimens with electric charged particle beams under a third control condition requiring that the magnification relative to the first image be smaller than the magnification of the second image; a step of image processing for analyzing the magnification of the first image to the specimen from the common field of view; a step of image processing for analyzing the magnification of the second image relative to the third image from the common field of view; and a step of calculating the magnification of the second image to the specimen from the magnification of the previous first image to the specimen, the magnification of the third image relative to the first image, and the magnification of the second image relative to the third image.

As one illustrative embodiment, it is preferable that in the electric charged particle beam microscopy, the image processing step includes a step of calculating the Fourier transform image of an image and a step of calculating the Fourier transformed image of the coordinate transformed image of the Fourier transformed image, the coordinate transformed image serving as the basis of calculating magnification.

As another illustrative embodiment, it is preferable that in the electric charged particle beam microscopy, the first control condition is a condition that makes it possible to measure the interval between crystal lattice surfaces from the image acquired, and the magnification for specimen is a magnification actually measured from the interval between lattice surfaces.

A second aspect of the present invention is directed to an electric charged particle beam application device which includes: an electric charged particle source for generating a first electric charged particle beam; a first electromagnetic field generator that leads the first electric charged particle beam to a specimen; a specimen stage for setting a position of a specimen with respect to the first electric charged particle beam; a detector for detecting secondary charged particles; a second electromagnetic field generator that leads the secondary charged particles radiating from the specimen to the detector; an image formation unit for forming an image of the specimen structure based on the detector output; and a controller for setting image magnification by using the electromagnetic field generator. The electric charged particle beam application device is preferably configured such that the controller has a magnification calibration unit; and magnification calibration unit records a first image with a known magnification by irradiating the specimen with an electric charged particle beam under a first control condition, records a second image having a common field of view with the first image by irradiating the specimen with the electric charged particle beam under a second control condition, calculates a magnification of the second image relative to the first image recorded, calculates a magnification of the second image from the magnification of the first image and the magnification of the second image relative to the first image, and records the magnification of the second image together with the second control condition.

As illustrative embodiments, in the electric charged particle beam application device, the controller sets the magnification by using a deflector that constitutes the first user interface for electromagnetic field generation; and the controller sets a magnification by using a lens that constitutes the second electromagnetic field generator.

A third aspect of the present invention is directed to a critical dimension measurement method for measuring the critical dimensions of a specimen to be measured by irradiating the specimen to be measured with an electric charged particle beam, detecting electrically charged particles secondarily generated from the specimen caused by the irradiation, and inputting the image data acquired into a computer. The method preferably includes: a step of inputting first image data including at least a standard specimen for magnification calibration into the computer; a step of calculating a magnification of the first image for the specimen by comparing an actual length of the standard specimen and a length on the first image; a step of inputting second image data including at least a specimen to be measured for critical dimension measurement into the computer; a step of calculating a magnification of the second image for the specimen by analyzing the magnification of the second image relative to the first image; and a step of converting a length of the specimen to be measured for critical dimension measurement on the second image into an actual length.

According to the critical dimension measurement method as described above, the magnification of the second image can be calibrated by analyzing the magnification of the second image for the first image, the magnification of which has been calibrated by using a standard specimen. Thereafter, the magnification of all of the images can be calibrated by repeating the calculation mentioned above by replacing the first image by the second image, and an improvement in the precision of critical dimension measurement can be expected.

A fourth aspect of the present invention is directed to a critical dimension measurement system which includes: a specimen stage for supporting a specimen to be measured and a standard specimen for calibration; an irradiation optical system for irradiating the specimen to be measured for critical dimension measurement or the standard specimen with an electric charged particle beam; a detector for detecting electric charged particles generated secondarily from the specimen to be measured for critical dimension measurement or the standard specimen as a result of the irradiation of the electric charged particle beam; a means for acquiring image signals from the detector; a magnification controller for setting a magnification of an image for a specimen by an adjustment of an electron optical system; an inputting means for inputting a magnification of an image to be taken; and a critical dimension measurement unit for measuring a length of a specimen from the image signal.

The critical dimension measurement system is preferably configured such that the magnification controller sets the electron optical system at the first and second magnification conditions in response to the image magnification inputted by the inputting means. Also, the critical dimension measurement system is preferably configured such that the critical dimension measurement unit calculates a magnification of the first image for the specimen by comparing an actual length of the standard specimen and a length on a first image by using the first image of the standard specimen taken under the first magnification condition, analyzes the magnification of a second image taken under the second magnification condition to thereby calculate a magnification of the second image for the specimen, and uses the magnification information to estimate a length of the specimen to be measured for critical dimension measurement.

A fifth aspect of the present invention is directed to a critical dimension measurement system which includes: an image signal formation unit for acquiring image signals for a specimen to be measured for critical dimension measurement by irradiating the specimen an with electric charged particle beam from an electric charged particle beam source, and detecting electric charged particles generated secondarily from the specimen; and a data processor for inputting image signals formed at the image signal formation unit, processing an image, and measuring a critical dimension of the specimen based on a result of the image processing. The critical dimension measurement system is preferably configured such that the data processor calculates a magnification of a first image for a specimen by comparing an actual length of a standard specimen and a length in the first image based on the first image of the standard specimen taken with a magnification under a first irradiation condition, analyzes a magnification of a second image taken under a second irradiation condition, calculates a magnification of the second image, and estimates a length of the specimen to be measured by using the magnification information.

The analysis of images taken and the actual measurement and calibration of the magnification of the images for the specimen on the whole range of magnification in accordance with the present invention can lead to a reduction in magnification errors. Any reduction in magnification errors results in an improvement of precision of measurement of the critical dimension of specimens.

The present invention as described above provides an improvement in the precision of the dimensional management of a large variety of industrial products on the nanometer scale and contributes to an improvement of the yield.

DETAILED DESCRIPTION OF THE PREFERRED EMBODIMENTS

First Embodiment

Figure 2:
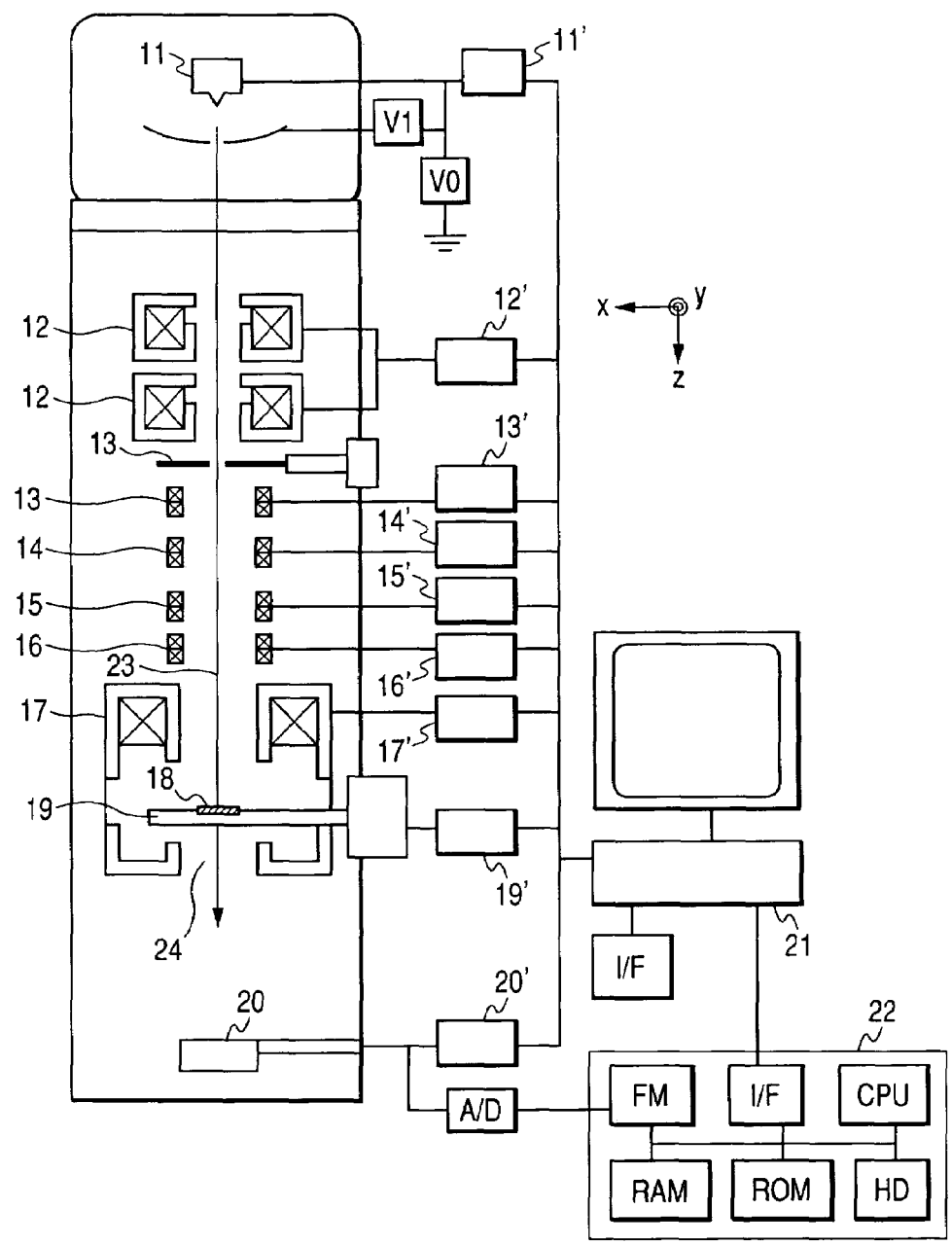
FIG. 2 is a diagram showing the basic configuration of a STEM.

The first embodiment of the present invention is directed to magnification calibration in a STEM. FIG. 2 is a diagram showing the basic configuration of the STEM used in the present embodiment. The configuration includes a control unit 11' for controlling the acceleration voltage and the emitting voltage of an electron gun 11, which produces the primary electron beam 23. A control unit 12' controls a condenser lens 12 for focusing the primary electron beam 12 and for controlling its amperage. Control unit 13' controls an alignment deflector 13 for adjusting the incident angle of the primary electron beam 23 incident upon the specimen 18 and for controlling its amperage. Control unit 14' controls stigmators 14 for adjusting the beam form of the primary electron beam 23 incident upon the specimen 18 and for controlling its amperage. Control unit 15'. Controls an image shift deflector 15 for adjusting the area of incidence of the primary electron beam 23 incident upon the specimen 18 and for controlling its amperage. Control unit 16' controls a scanning deflector 16 for raster scanning the primary electron beam 23 incident upon the specimen 18 and for controlling its amperage. Control unit 17' controls an objective lens 17 for adjusting the focus position of the primary electron beam 23 for the specimen 18 and for controlling its amperage. Control unit 19' controls a specimen stage 19 for setting the position of the specimen 18 in the specimen chamber and by controlling its position. Control unit 20' for controlling an electron detector 20 for detecting the electron beam 24 having passed through the specimen and its gain and offset. A computer 21 loaded with a STEM control program; and a computer 22 loaded with an image processing program. Each control unit is command controlled by the computer 21. The function of the computers 21 and 22 can be performed by a single computer. In the configuration shown in FIG. 7, the computers 21 and 22 can be identified as constituting a data processor and the other constituent elements necessary to operate as an image signal processing unit.

First of all, the step of acquiring STEM images by using the apparatus shown in FIG. 2 will be described. The electron gun 11 emits the primary electron beam 23 in response to an emitting voltage of V1 and an applied acceleration voltage of V0. The direction nearly parallel with the optical axis of a mirror is defined as the Z direction, and the plane nearly orthogonal with the optical axis is defined as the XY plane. A thin film forming specimen 18 is placed on the specimen stage 20, and the primary electron beam 23 is emitted in the Z direction. The primary electron beam 23 is focused to the nm order by using a condenser lens 12. A scanning deflector 16 is used to raster scan on the specimen 18. When the primary electron beam 23 is emitted towards the thin film specimen 18, most of the electrons pass through the specimen 18. This transmission electron beam 24 is detected by an electron beam detector 20, and it is synchronized with the electron beam scanning signals of the scanning deflector 16 to form a STEM image.

The magnification of the STEM image of the specimen is set by the amplitude of the electric current of the scanning deflector 16. The electron beam scanning area is actually measured by using a standard specimen, including a structure of known dimension, and a desired magnification is set by adjusting the width of the current of the scanning deflector 16. However, the range of magnification in which the scanning area can be actually measured by using a standard specimen is very limited. Specifically, the specimens which may be used for calibration of magnification for a low magnification include carbon grating and mesh. Magnification is calibrated by using a pitch pattern of known cycle contained in these specimens. The cycle of the pitch pattern that can be created by the present processing technology is several hundreds of nm. In order to average the processing errors, images containing 10 or more pitch patterns are taken, and their critical dimension is measured from the Fourier transform image thereof, respectively. The magnification at which approximately 10 pitch patterns are contained is approximately 10,000 times. A lattice image is used for the calibration of magnification at a high magnification. Lattice intervals vary between 0.102 nm for a gold single crystal at the narrower limit and 1.0 nm for a mica single crystal at the wider limit, and the magnification at which a lattice image can be observed is several millions of times or more. Since the magnification cannot be calibrated between 10,000 times and a million times by using a standard specimen, up to now the magnification has been calculated based on the relationship between the magnification calibrated by the standard specimen and the amplitude of electric current by assuming that there is a parallel relationship between the amplitude of the electric current of the scanning deflector 16 and the scanning range of incident electron beams.

As described above, the magnification can only be calibrated by use of the images actually taken within a limited range of magnification. Since, at other magnifications, the magnification of an image of a specimen is calculated from the control current of the scanning deflector 16, any magnification contains errors of approximately ±5%. This is due to the fact that there is, strictly speaking, no relationship of proportionality between the amplitude of the electric current and the range of scanning. Furthermore, the proportionality coefficient between the amplitude of the electric current and the range of scanning varies depending on the emitting condition of electrons from the electron gun 11, the non-linearity of the electromagnetic field due to the action of the condenser lens 12 and the objective lens 17, the height of specimen within the lens, etc.

Figure 1:
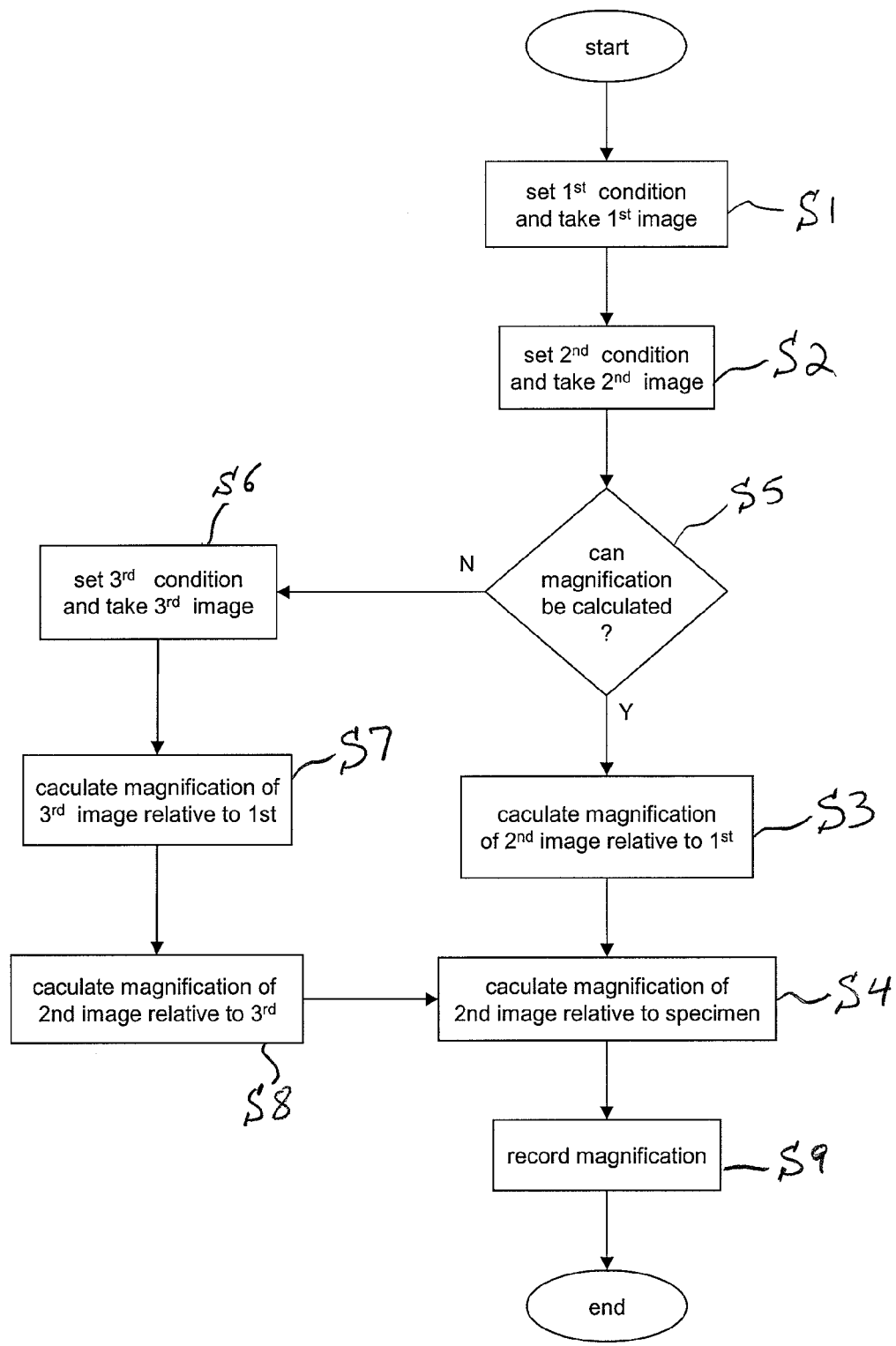
FIG. 1 is a flowchart showing a process of analyzing the magnification of images for a specimen.

In accordance with the present invention, in order to improve the precision of setting of the magnification, images are actually taken at all magnifications, and the magnification is analyzed from the images taken in order to perform calibrations. A specific process of magnification analysis is shown in FIG. 1. A first image of which the magnification for the specimen is measured by using a standard specimen having a known cycle of repetition is recorded (S1). Next, a second image at any freely chosen magnification is recorded (S2). The magnification of the second image relative the first image is analyzed by using image analysis processing (S3), and the magnification of the second image relative to the specimen is calculated (S4). Thereafter, magnification on the whole range of the electron microscope is analyzed by using images actually taken by repeating the above-mentioned analyses of magnification by taking the second image as the first image of which the magnification for the specimen is known. Magnifications actually measured are recorded together with the control conditions of the electron microscope and the magnifications are calibrated. These steps make it possible to improve, by a digit, the precision of magnification of the electron microscopes.

Figure 4:
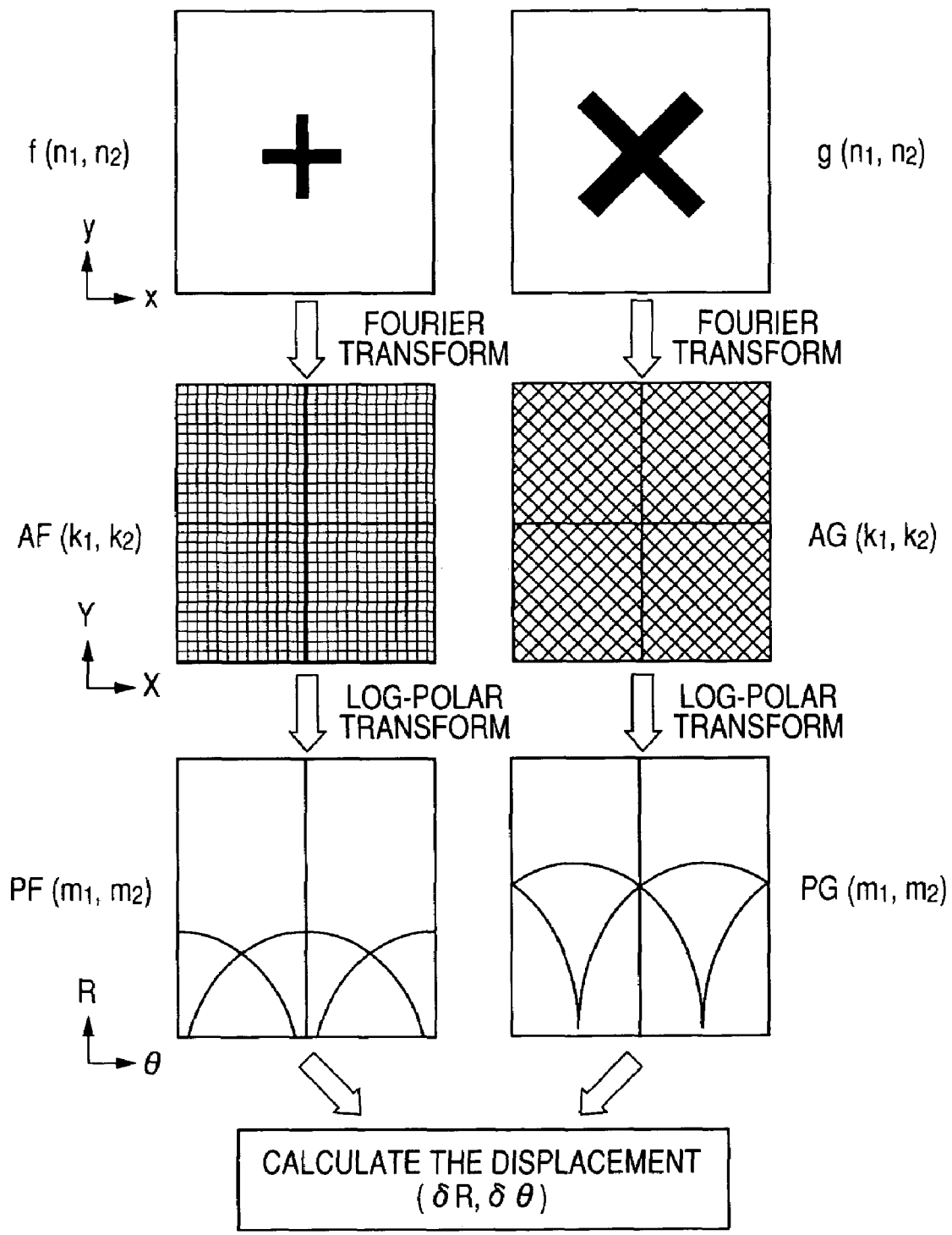
FIG. 4 is a diagram showing a step of transforming the rotation and magnification of an image into parallel movements.

In the present embodiment, the following magnification analysis method is adopted. The analysis of magnification consists of a step of converting the rotation and magnification of an image into parallel movements and a step of analyzing the displacement between transformed images. To begin, the step of transforming the rotation and magnification of an image into parallel movements will be described with reference to FIG. 4. Suppose the input image is a discrete image of N×N pixels $f(n_1, n_2)$, $g(n_1, n_2)$. Each image is a discrete Fourier transformed as shown in the following formula Number 1 to acquire a frequency spectrum.

$$F(k_1, k_2) = F[f(n_1, n_2)]$$

$$G(k_1, k_2) = F[g(n_1, n_2)]$$

Numerical expression 1

Just as shown in the following formulae Number 2, the formulae are rearranged in such a way that the zero frequency components of F and G may appear in the middle of the image.

$$CF(k_1, k_2) = F\left(\left(k_1 + \frac{N}{2}\right) \bmod N, \left(k_2 + \frac{N}{2}\right) \bmod N\right)$$

$$CG(k_1, k_2) = G\left(\left(k_1 + \frac{N}{2}\right) \bmod N, \left(k_2 + \frac{N}{2}\right) \bmod N\right)$$

Numerical expression 2

The amplitude spectrum of CF and CG is calculated as shown in the following formula Number 3. As the amplitude spectrum contains no information relating to the parallel movement of images $f(n_1, n_2)$, $g(n_1, n_2)$, AF and AG will be quantities not dependent on parallel movements.

$$AF(k_1, k_2) = |CF(k_1, k_2)|$$

$$AG(k_1, k_2) = |CG(k_1, k_2)|$$

Numerical expression 3

AF and AG are Log-Polar transformed. The results of transformation are shown in the following formula Number 4.

$$PF(m_1, m_2) = AF\left(\frac{N}{2} + r_{m1}\cos\theta_{m2}, \frac{N}{2} + r_{m2}\sin\theta_{m1}\right)$$

$$PG(m_1, m_2) = AG\left(\frac{N}{2} + r_{m1}\cos\theta_{m2}, \frac{N}{2} + r_{m2}\sin\theta_{m1}\right)$$

Numerical expression 4

Provided, however, that $r_{m1}$ and $r_{m2}$ are as shown in the following formula Number 5.

$$\begin{cases} r_{m1} = \frac{1}{2}N^{\frac{m_1}{N}} \\ \theta_{m2} = \frac{m_2}{N}\pi \end{cases}$$

Numerical expression 5

Assuming an equation Number 6 here, one gets a formula Number 7, which leads to a formula Number 8.

$$g(k_1, k_2) = f(\alpha k_1, \alpha k_2)$$

Numerical expression 6

$$G(n_1, n_2) = \frac{1}{\alpha}F\left(\frac{n_1}{\alpha}, \frac{n_2}{\alpha}\right)$$

Numerical expression 7

$$PG(m_1, m_2) = \frac{1}{\alpha^2}PF\left(\frac{N}{2} + \frac{N^{\frac{m_1}{N}}}{2\alpha}\cos\theta_{m2}, \frac{N}{2} + \frac{N^{\frac{m_1}{N}}}{2\alpha}\sin\theta_{m2}\right)$$

Numerical expression 8

The introduction of τ satisfying the equation of the following formula Number 9 in formula Number 8 leads to the following formula Number 10.

$$\alpha = N^{\frac{\tau}{N}}$$

Numerical expression 9

$$PG(m_1, m_2) \frac{1}{\alpha^2}PF\left(\frac{N}{2} + \frac{N^{\frac{m_1-\tau}{N}}}{2}\cos\theta_{m2}, \frac{N}{2} + \frac{N^{\frac{m_1-\tau}{N}}}{2}\sin\theta_{m2}\right) = \frac{1}{\alpha^2}PF(m_1 - \tau, m_2)$$

Numerical expression 10

The formula Number 10 transforms a magnification a in the actual space into a parallel movement in the $m_1$ direction. Any rotation in the actual space is transformed into parallel movements in the $m_2$ direction. Displacements between PG and PF are analyzed and transformed into magnification and rotation in order to calculate magnification and rotation. The use of LG and LF resulting from the logarithmic transformation of AF and GF as shown in the following formula Number 11 in the place of AG and AF results in an improvement in the precision of calculation. This contributes to an emphasis of the high frequency components of amplitude images of AG and AF.

$$LF(k_1, k_2) = \log(AF(k_1, k_2) + 1]$$

$$LG(k_1, k_2) = \log(AG(k_1, k_2) + 1]$$

Numerical expression 11

Figure 5:
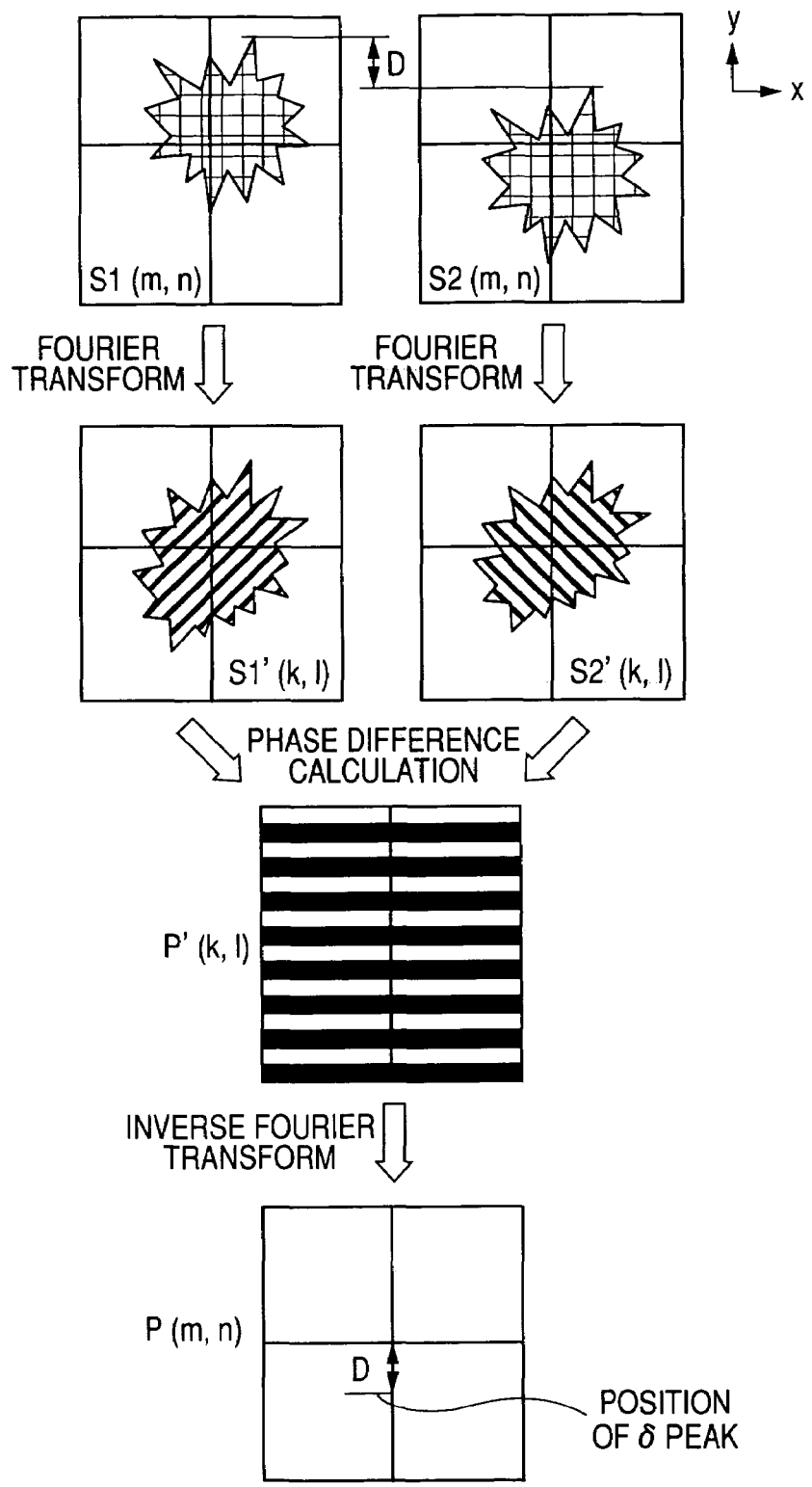
FIG. 5 is a diagram showing calculation steps of the displacement analysis method.

Now, the displacement analysis method will be described with reference to FIG. 5. Assuming two discrete images S1 (n, m) and S2 (n, m) containing displacements $D=(D_x, D_y)$, which are described as $S1(n, m)=S2(n+D_x, m+D_y)$, a two-dimensional discrete Fourier transformation of S1 (n, m) and S2(n, m) results in S1'(k, l) and S2'(k, l). Since Fourier transformation involves a formula $F\{S(n+D_x, m+D_y)\}=F\{S(n, m) \exp(iD_x \cdot k + iD_y \cdot 1)\}$, this formula can be metamorphosed into $S1'(k, 1)=S2'(k, 1) \exp(iD_x \cdot k + iD_y \cdot 1)$. In other words, the displacement of S1'(k, l) and S2'(k, 1) is expressed by a phase difference $\exp(iD_x \cdot k + iD_y \cdot 1)$. Since P'(k, l) is also a wave whose cycle is $(D_x, D_y)$, δ peaks develop even at the position of $(D_x, D_y)$ on the analysis image P(n, m) resulting from the inverse Fourier transform of a phase difference image P' (k, l). Even when, instead of wholly removing the amplitude information, an image in which an amplitude component is restricted by processing the amplitude component of $S1'(k, 1) \cdot S2'(k, 1)* = |S1||S2'| \exp(iD_x \cdot k + iD_y \cdot 1)$ with log or $\sqrt{}$ is calculated and an inverse Fourier transform is carried out on the image, a δ peak develops at the positions $(D_x, D_y)$ of displacement vector. Therefore, the image may be subjected to a displacement analysis. Since a δ peak develops at the positions $(-D_x, -D_y)$ even by Fourier transforming the phase difference image P'(k, l), a Fourier transformed image of the phase difference image P'(k, l) may be subjected to a displacement analysis.

As it is possible to assume that only δ peaks exist in the analysis image P (n, m), the position of δ peak can be determined with a precision of less than a decimal point by calculating the position of the gravity center or fitting coefficients. And, since anything other than δ peaks can be regarded as noises, the proportion of the intensity of δ peaks to the intensity of the whole analysis image (n, m) can be regarded as a degree of agreement between the images. Prior displacement analysis methods made it difficult to assess the reliability of the results of displacement analysis. Even when a wrong displacement value is outputted due to insufficiency of the frequency components necessary for the analysis, the displacement information serves as a basis of the analysis and calibration process that will be undertaken.

According to the present displacement analysis method, the degree of agreement is outputted, and the function of setting the minimum value of agreement and automatically taking the necessary measures, such as retaking the image, is provided when the degree of agreement is below the lower limit. Specifically, the judgment step (S5) is provided as shown in FIG. 1. When it is determined that the magnification of the second image for the first image cannot be analyzed, a third image whose magnification difference is smaller than that of the second image relative to the first image is used (S6) to analyze the magnification of the third image relative to the first image (S7), and to analyze the magnification of the second image relative to the third image (S8). Then, both magnifications are multiplied to calculate the magnification of the second image relative to the first image. When it becomes impossible to analyze a blurred image due to contamination, even when the magnification of the third image relative to the first image approaches 1, defocusing or coming out of the field of view due to mechanical errors of the apparatus are likely causes. With regard to impediments previsible from the beginning, such as contamination, prior measures should be taken. For example, a plurality of fields of view used for analysis will be registered, and when it is determined that it is difficult to implement analysis with the field of view used at the beginning, another analysis will be undertaken with another field of vision that has been registered. When the cause cannot be specified even when the measures mentioned above have been taken, an error message is displayed and the analysis is terminated.

In analyzing the magnification of the second image for the first image, any area not common between the images constitutes an impediment for the analysis of the image, and therefore it is preferable to delete as much as possible such disparate areas. There are two preprocessing methods that may be used for this purpose. The first preprocessing method is a method of enlarging or reducing the first or second image in advance so that the magnification of the second image for the first image may approach 1. The second preprocessing method is a method of masking areas other than the common areas.

And, when the magnification difference between images is too large, sometimes it becomes impossible to analyze the magnification. For example, in a general-use apparatus, the number of pixels of an image to be taken is approximately 1,024×1,024. For the analysis of magnification, a number of pixels of at least approximately 128×128 is necessary. In this case, when the difference of magnification is set at eight times or more, the analysis of magnification seems to become difficult. When the first preprocessing mentioned above is performed, the first image is reduced to 128×128 pixels, and from the area common to the first image and the second image, images of 128×128 pixels are cut out, and the magnification of both images is analyzed. When the difference of magnification is eight times or more, it becomes necessary to cut out a part common with the first image from the second image and to enlarge images while interpolating the same. It is obvious that a difference develops in the amount of information contained in the images even in the case of images taken of the same area. The question of whether it is possible to analyze the magnification or not depends on the structure of the specimen used in taking the images. Therefore, the first image and the second image are taken by an appropriate difference of magnification, for example, five times approximately, and it will be determined whether the analysis of magnification is possible or not by using the judgment process by the degree of agreement described above. When the analysis of magnification is impossible, the third image whose difference of magnification relative to the first image is smaller than that relative to the second image is used to analyze the magnification of the first image and the third image, and the magnification of the second image relative to the third image is analyzed. From the result of these analyses, the magnification of the second image relative to the first image is obtained.

Figure 9A:
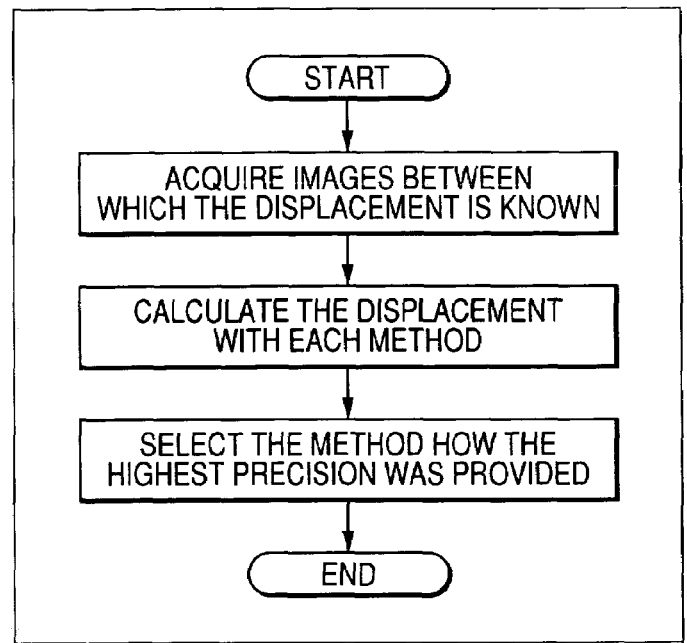
FIG. 9A is a flowchart showing the procedure for selection of analysis methods, wherein a displacement analysis method is adopted.

In addition, for the magnification analysis method, methods other than the one described above may be used. For example, the standardization mutual correlation method or the minimum involution method may be used as a displacement analysis method. Depending on the images, often no analysis can be made by the displacement analysis method based on phase, but other analysis methods often make it possible to carry out the same. It is also possible to determine automatically which displacement analysis method should be adopted. The procedure is shown in FIG. 9A. Two images between which the displacement is known are prepared. For example, two images containing a displaced position are cut out from a single image. The displacement between images is calculated by the displacement analysis method based on phase, the standardization correlation method, the minimum involution method and the like. The method by which the most precise calculation result has been obtained should be adopted.

Figure 9B:
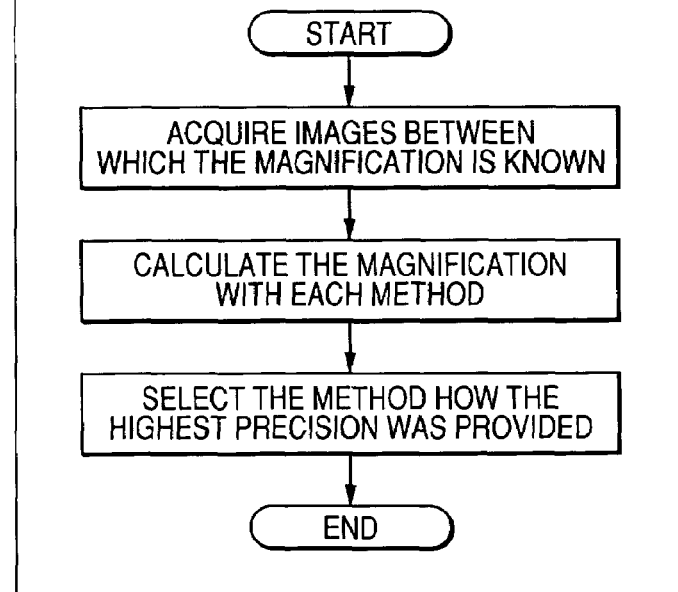
FIG. 9B is a flowchart showing the procedure for selection of an analysis method, wherein magnification analysis method is adopted.
Figure 10:
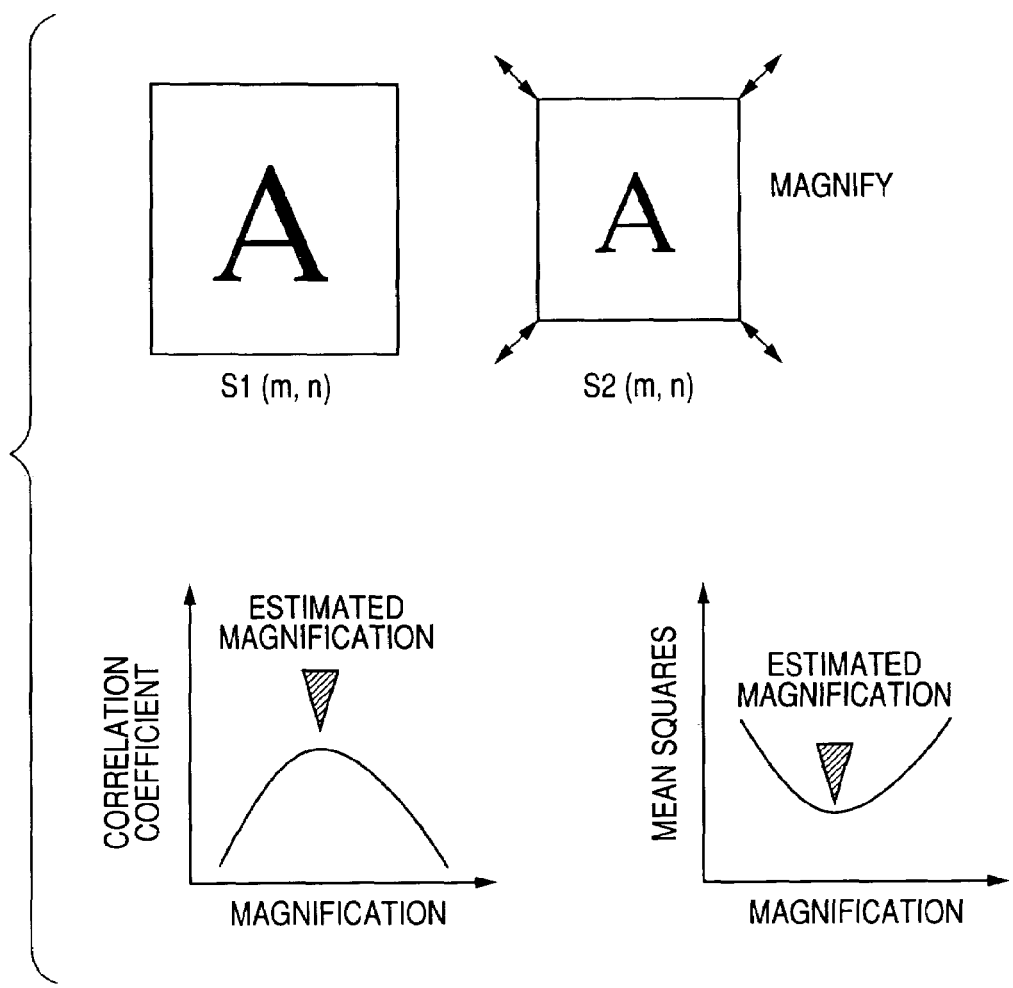
FIG. 10 is a diagram for illustrating a magnification analysis method.

A method not based on Log-Polar transform may also be used to analyze the magnification. For example, the method shown in FIG. 10 may be used for analysis. The magnification in one image is changed in the computer and the correlation value with another image shown in the following formula Number 12 is calculated. Since the correlation value takes the maximum value when the two images agree, the magnification at the time when the correlation value is the maximum is specified as the analysis result. The minimum involution method shown in the following formula Number 13 may be used in place of the correlation value. The minimum involution method takes the minimum value when the two images agree. The magnification at the time when the minimum involution becomes the minimum is specified as the result of analysis. Alternatively, the following formula Number 14 may be used. In this case also, the value becomes the minimum when the two images agree. The question of which magnification analysis method should be chosen can be automatically determined in the process shown in FIG. 9B. In other words, images whose magnification is known are prepared. For example, two images with different magnifications are produced from a single image, and their magnification is analyzed by various magnification analysis methods, and the method by which the most precise analysis result has been obtained is chosen.

$$C = \frac{F(k_1, k_2) \cdot G(k_1, k_2)}{|F(k_1, k_2)| \cdot |G(k_1, k_2)|} \qquad \text{Numerical expression 12}$$

$$Q = \frac{|f(n_1, n_2) - g(n_1, n_2)|^2}{|f(n_1, n_2)| \cdot |g(n_1, n_2)|} \qquad \text{Numerical expression 13}$$

$$Q' = \frac{\sum |f(n_1, n_2) - g(n_1, n_2)|}{\sum |f(n_1, n_2)| \cdot \sum |g(n_1, n_2)|} \qquad \text{Numerical expression 14}$$

Figure 3A:
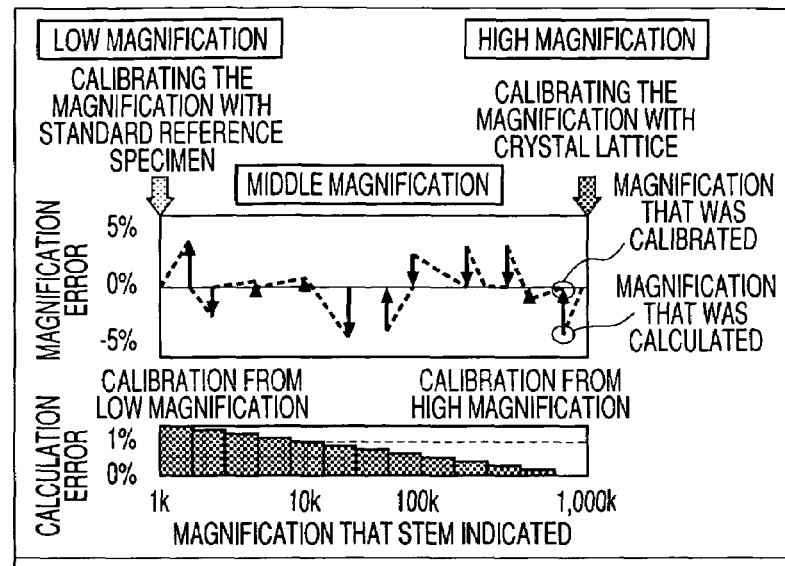
FIG. 3A is a diagram showing the accumulation of analytical errors due to multistage magnification calibration, when an analysis of magnification is undertaken from a high magnification to a low magnification.
Figure 3B:
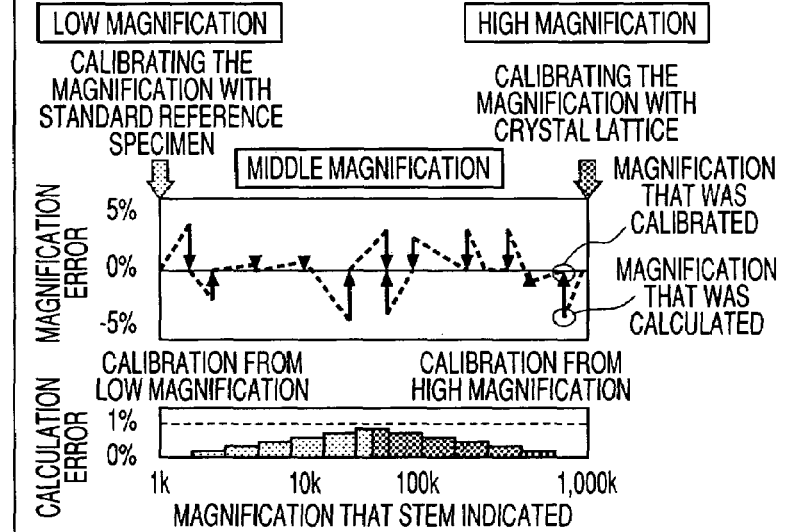
FIG. 3B is a diagram showing the accumulation of analytical errors due to multistage magnification calibration, when an analysis of magnification is undertaken from a high magnification to a middle magnification and then from a low magnification to a middle magnification.
Figure 3C:
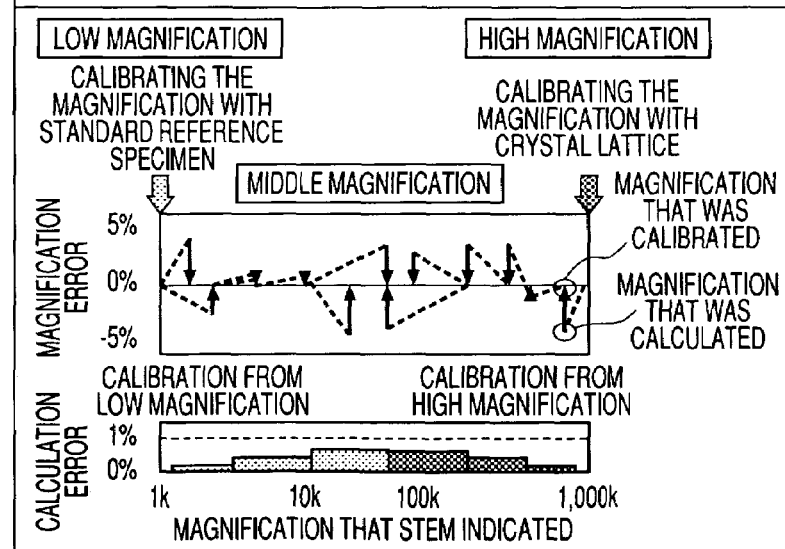
FIG. 3C is a diagram showing the accumulation of analytical errors due to multistage magnification calibration, when an analysis of magnification is undertaken by changing the magnification intervals.

And now the procedure for magnification analysis will be described. As described above, due to a wide range of STEM spanning from 10,000 times to a million times, where magnification cannot be calibrated by using a standard specimen whose repetition cycle is known, it is necessary to implement magnification analyses by an image process in multiple stages. As the number of magnification analyses increases, analysis errors are accumulated. In order to minimize the accumulation of analysis errors, the analysis precision must be improved and the number of analyses must be reduced. It is possible to reduce the number of analyses effectuated from the magnification calibrated by the standard specimen until the time when the desired magnification is reached by using one's ingenuity on the analysis process. Instead of proceeding to analysis in one direction from a high magnification to a low magnification and cross-checking with the standard specimen of a low magnification, as shown in FIG. 3A, it is better to proceed to analysis in two directions as shown in FIG. 3B (e.g., to proceed to analyses from a high magnification to a middle magnification and from a low magnification to a middle magnification and to cross-check at a middle magnification). In this way, the level of accumulation of magnification errors can be minimized. In addition, as shown in FIG. 3C, it is better at first to analyze magnification at a rough magnification interval and then analyze magnification by setting, for the magnifications in between, the analyzed images as the first image. In this way, the number of analyses from the magnification calibrated by the standard specimen to the desired magnification can be reduced.

While the number of analyses can be reduced by increasing the magnification difference between images, there is a concern that the common structure among images would diminish and the precision of analysis may worsen. In other words, when the magnification difference is increased, the number of analyses decreases, but the number of respective analysis errors increases. When the magnification difference is decreased, the number of analyses increases, but the number of respective analysis errors increases. When analysis errors can be roughly estimated, this is used for choosing the analysis process. For example, in the method of transforming magnification and rotation into parallel movements and of analyzing displacement by an analysis method based on phase, it is possible to estimate analysis errors from the δ peak intensity or degree of agreement. Specifically, in case of standardization by taking the degree of agreement, when two images, each having 128×128 pixels, agree, as 100, and the degree of agreement, when they are completely different, as 0, although the analysis error is 0.1 pixel or less when the degree of agreement is 30 or more, the analysis errors gradually increase when the degree of agreement falls to 30 or less, and the analysis errors grow to approximately 0.3 pixels when the degree of agreement falls to 10 or less. Magnification analyses are undertaken when the magnification difference is set a high level and when it is set at a low level, and the accumulation of analysis errors is estimated from the degree of agreement, and the one for which accumulation of analysis errors is small is chosen.

The optimum magnification analysis process depends on the specimen structure used in the analysis. In order to examine the optimum analysis process, it is necessary to store the images taken in a hard disk. On the other hand, in the case of analysis by a specimen structure for which the optimum analysis process is specified, it is more efficient to alternatively carry out the taking of images and analysis, instead of storing images in a hard disk. Images taken are recorded in the first place in a frame memory. Images are analyzed there and only the analysis results are stored. Then, the images are deleted. Generally, due to a slow speed of recording in a hard disk, a higher efficiency can be achieved by recording only the analysis results without storing images.

The procedure for taking images used in the magnification analysis will now be described. Magnification analysis requires the existence of a common structure among images. In other words, it is necessary to irradiate the same area with an electron beam. The irradiation by an electron beam for a long time results in contamination of the irradiated area. The higher the magnification is, the more contamination occurs. And the higher the magnification is, the greater will be the effect of a blurred image due to contamination. It is generally difficult to take a lattice image in a contaminated area. Therefore, it is better to begin taking images at a high magnification and keep on taking images by gradually reducing the magnification.

Figure 6:
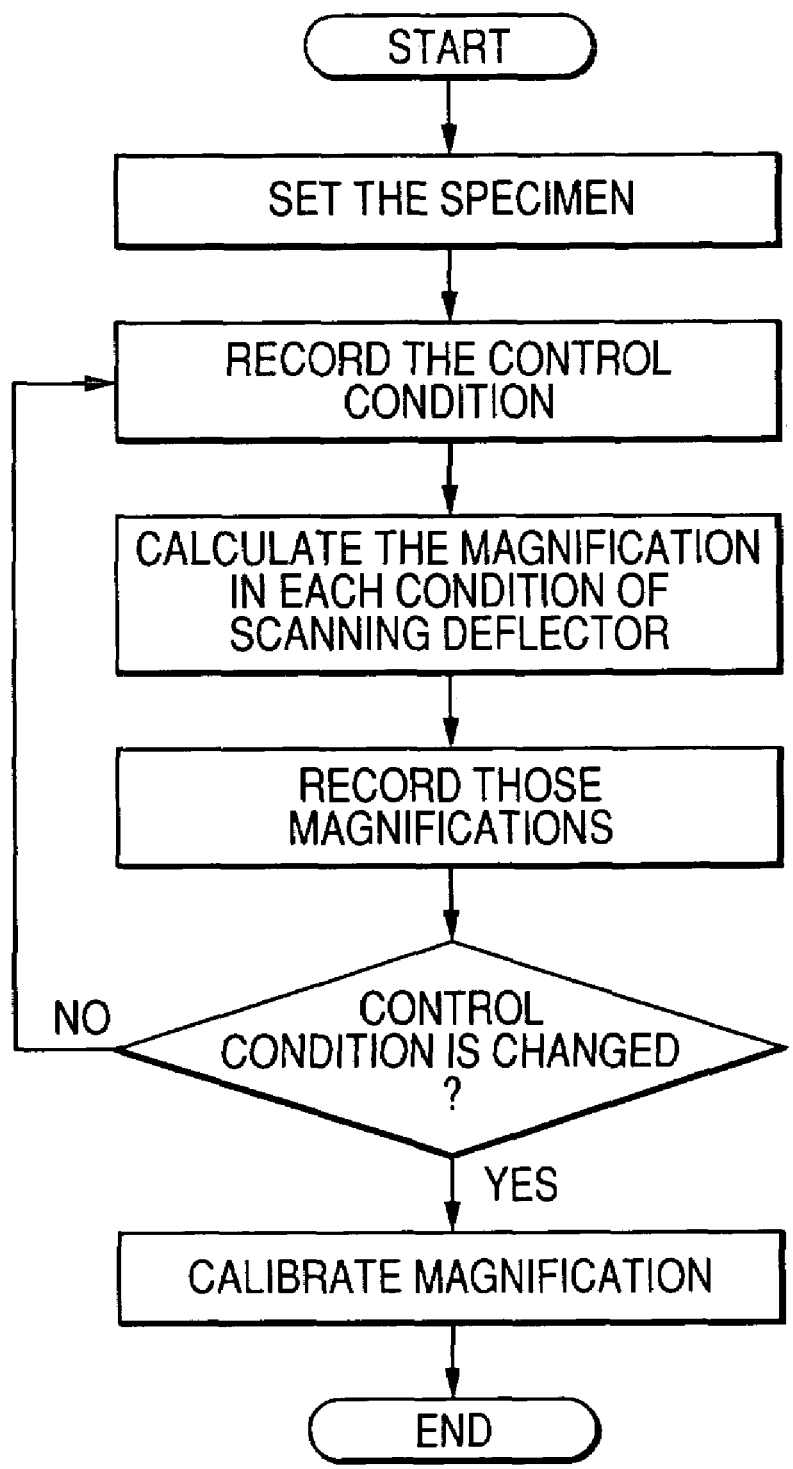
FIG. 6 is a flowchart showing the procedure of calibrating the magnification of an apparatus in the whole range of magnification.

The procedure for calibrating the magnification of an apparatus in the whole range of magnification by using the magnification analysis technique described above is shown in FIG. 6. To begin, a specimen for calibrating the magnification is chosen. One of the conditions is that images having a suitable frequency component may be taken so that images are even taken at magnifications ranging from several hundreds of times to several millions of times. This is because magnification calibration cannot be undertaken with similar images or blurred images. Specimens, of which only similar images can be taken at high magnifications due to the absence of fine structure and only similar images can be taken at low magnifications due to their too small size, are unsuitable. The second condition is that they contain a structure having a known repetition cycle. It is desirable that they contain a structure for low magnification and high magnification. For example, specimens made by depositing gold and the like on carbon grating or specimens made by depositing gold and the like on microgrit are suitable. Carbon grating has traditionally been used for calibrating magnification at low magnifications, and the interval between lattices of gold has been used for calibrating magnification at high magnifications. Deposited gold particles are arranged amorphously, and images having a suitable frequency component can be acquired at any magnification. Microgrit is a specimen formed by depositing a thin film of carbon on mesh, and the mesh may be used for calibrating magnification at low magnifications, while the interval between lattice fringes of gold may be used for calibrating magnification at high magnifications. On the other hand, because of the narrow interval between lattice fringes of gold, materials such as carbon graphite that can be easily used by beginners for taking a lattice image may be attached to carbon grating or microgrit. Specimens having a pitch pattern whose repetition cycle is several hundreds nm and a structure from several nm to several tens of nm, for example, specimens made by transforming into a thin film semiconductor Si device including a film oxide or polycrystalline structure for use in a TEM, are suitable. For calibration at low magnifications, the pitch pattern is used. For calibration at high magnifications, the interval between lattice fringes of Si is used. The dimension of the device structure which depends on the controllability of the manufacturing apparatus is unsuitable for calibration of the magnification. However, it is necessary as a reference structure in the image analysis at a middle magnification.

Then, the apparatus conditions for the calibration of magnification are set. The magnification of a STEM is affected by the acceleration voltage VO, the emitting condition of electrons from an electron gun 11, the non-linearity of the electromagnetic field due to a condenser lens 12 and an objective lens 17, the height of the specimen in the lens and the like. An acceleration voltage VO is applied to the mirror body, and VO is recorded. If the electron source is the same, the emitting condition of the electron beam from the electron gun 11 can be monitored from the emitting voltage V1, and after adjusting the amperage of the primary electron beam 23 on the basis of the emitting voltage V1, the value of the emitting voltage V1 is recorded. In order to monitor the electromagnetic field created by the condenser lens 12, the excitation current of each lens is recorded. In order to keep the electromagnetic field as much as possible at a constant condition, the alignment of the axis should be completed. Since the height of specimen can be monitored from the excitation current of the objective lens 17 in the just focus condition, the excitation current of the objective lens 17, while the specimen 18 is in focus, should be recorded. In addition, in an electron microscope in which the electron beam scanning speed can be set from high speed to low speed, the scanning signals generation unit may be different depending on high speed and low speed operation. In this case, the electron beam scanning speed should also be recorded.

The first image, including a lattice image, is taken at a high magnification, and the interval between lattice fringes is analyzed by Fourier transforming the first image, and the magnification of the first image relative to the specimen is analyzed. Then, the scanning range is expanded by reducing the magnification (i.e., by increasing the current amplitude of the scanning deflector 16), and the second image is taken. In order to facilitate calibration of the magnification after the analysis, it is better to maintain apparatus parameters other than the scanning deflector 16 at constant levels. The image analysis described above leads to the actual measurement of the second image relative to the specimen. The magnification of the second image relative to the specimen is stored together with the apparatus parameters at the time of taking the second image. Thereafter, the magnification analysis is repeated by taking the second image, for which the magnification analysis has been completed, as the first image, of which the magnification relative to specimen is known.

After actually measuring the relationship between the current amplitude of the scanning deflector 16 in a certain apparatus condition and magnification, the question of whether the relationship between the current amplitude of the scanning deflector 16 in another apparatus condition and magnification should be actually measured is decided. Since the setting of the condenser lens 12, the electron beam scanning speed and other modes have been set in advance, the magnification is analyzed and calibrated in each mode. Since the emitting voltage V1 and the height of the specimen in the lens are continually set, after magnification analysis at some set values, magnification is calibrated by using the interpolating values of the same. When the apparatus condition data necessary for the magnification calibration has been measured, the analysis is terminated, and magnification is calibrated based on the data acquired.

The specific method of magnification calibration includes the method of reflecting on the control current of the scanning deflector 16 and the method of reflecting the result of magnification analysis and images on the scale bar displayed and magnification displayed. In the calibration of an apparatus, in order to improve the future operability, it is better to have the analysis result reflected on the control current of the scanning deflector 16.

As described above, in addition to calibrating the magnification for all range of magnification in the whole apparatus setting conditions, the need for specific magnification calibration is also high. This is because the magnification obtained by actually measuring images taken is more precise than the magnification obtained from apparatus conditions.

In a specific magnification calibration, apparatus parameters other than the scanning deflector 16 are kept as much as possible at a constant level, and images are successively analyzed from the magnification, including the structure with a known cycle of repetition to the magnification at which measurement of a dimension is desired to proceed to the magnification calibration. For example, when the dimension of a semiconductor device is to be measured by using a sectional specimen of the device, the lattice image of the Si substrate is taken as the first image, the magnification of the first image for the specimen is analyzed. The magnification is successively analyzed by reducing the magnification to the level of magnification at which the desired dimension is to be measured. After completing the calibration of magnification, the desired dimension is measured. A pitch pattern whose cycle in the semiconductor device is known is also taken at a low magnification as the first image, the magnification of the first image for the specimen is analyzed, and the magnification is successively analyzed by increasing the magnification up to the magnification at which measurement of a dimension is desired for the calibration of magnification. In specific magnification calibration, it is better to calibrate magnification than to change the extent of scanning of the scanning deflector 16. In other words, it is better to have the analysis result reflected on the displayed magnification or scale bar than to change the apparatus conditions, because any change in the apparatus conditions can cause slight changes in the magnification.

Figure 11:
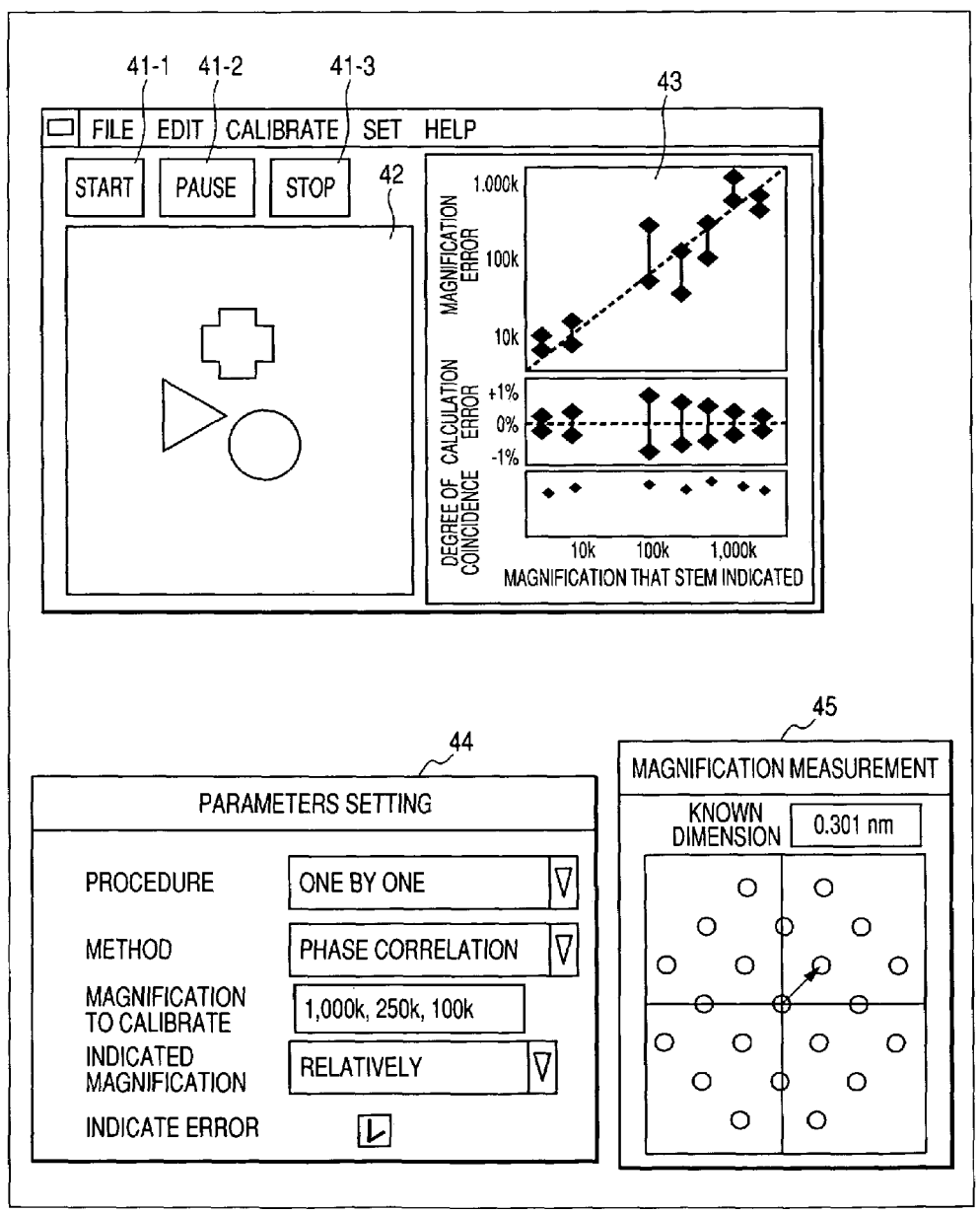
FIG. 11 is a diagram showing a user interface for process control for controlling the progress of a process in a magnification analysis.

In a specific magnification analysis, it is necessary to choose the areas to be used in the first image and the areas in which measurement of dimensions is desired by responding to the user's needs. Since the precision of magnification required varies depending on the user's needs, it is better to make an arrangement to make it possible to set images taken or analysis parameters according to the user's needs. FIG. 11 shows an example of an image displayed by the computers 21 and 22. In the user interface shown in FIG. 11, parameters are set and analysis results are confirmed. The image includes a process control window 41 for controlling the progress of a process, including <start>, <pause> and <stop> buttons, an image indication window 42 for indicating the image being taken or analyzed, and a result and error indication window 43. <Start> is the start instruction button of the magnification calibration (auto scaling) process described above. The parameter setting box 44 is used with a very different frequency of use depending on the user, and, therefore, the box should be designed to pop up whenever necessary. The magnification measurement window 45 for analyzing the magnification of the first image for the specimen from the pitch pattern should also be prepared. The Fourier transform image of the pitch pattern should be displayed, and the pitch pattern spot used in magnification calibration should be chosen from the spots appearing on the Fourier transform image. The question of whether the spot corresponds to the pitch pattern or not can be confirmed in the image resulting from the inverse Fourier transform of an image that is masked on the area other than the spot. It is also preferable to create a function of specifying the center of the spot by calculating the center of gravity or by fitting a coefficient when the user has chosen an area including the spot. The reciprocal of the spot position is the pitch pattern interval, and the magnification at which this interval turns into a known interval is calculated.

After the indication of analysis errors is checked in FIG. 11, the analysis errors are indicated in the result and error indication window 43. The analysis errors are such analysis errors as are described with reference to FIG. 3A through FIG. 3C.

In order to further improve the precision of dimensions, the direction of placing a specimen is important. Since an electron advances spirally in the mirror body, a change in the setting of the condenser lens 12 and the objective lens 17 causes the image to rotate. The rotation of an image causes the direction of measuring dimensions to slip and results in a discrepancy in the measurement results. According to the magnification analysis method used this time, the magnification and rotation speed are calculated at the same time. It is preferable to calibrate in such a way that the direction of the image may be constant by using the raster rotation of the rotating image by storing the magnification and rotation angle and by adjusting the ratio of current flowing in the XY plane of the scanning deflector 16. This calibration is indispensable when the setting of the condenser lens 12 and the objective lens 17 has been changed, rather than when the setting of the scanning deflector 16 has been changed, in other words when the magnification has been changed. Rotation should be calibrated in such way that the rotation angle to the first image may be zero, taking the direction of rotation in the first image as a reference. The calibration of the rotation procedure can be executed by replacing "magnification" shown in FIG. 6 with "magnification and rotation." As for analyses between various images, it is enough to replace "magnification" shown in FIG. 1 with "magnification and rotation."

Second Embodiment

Figure 7:
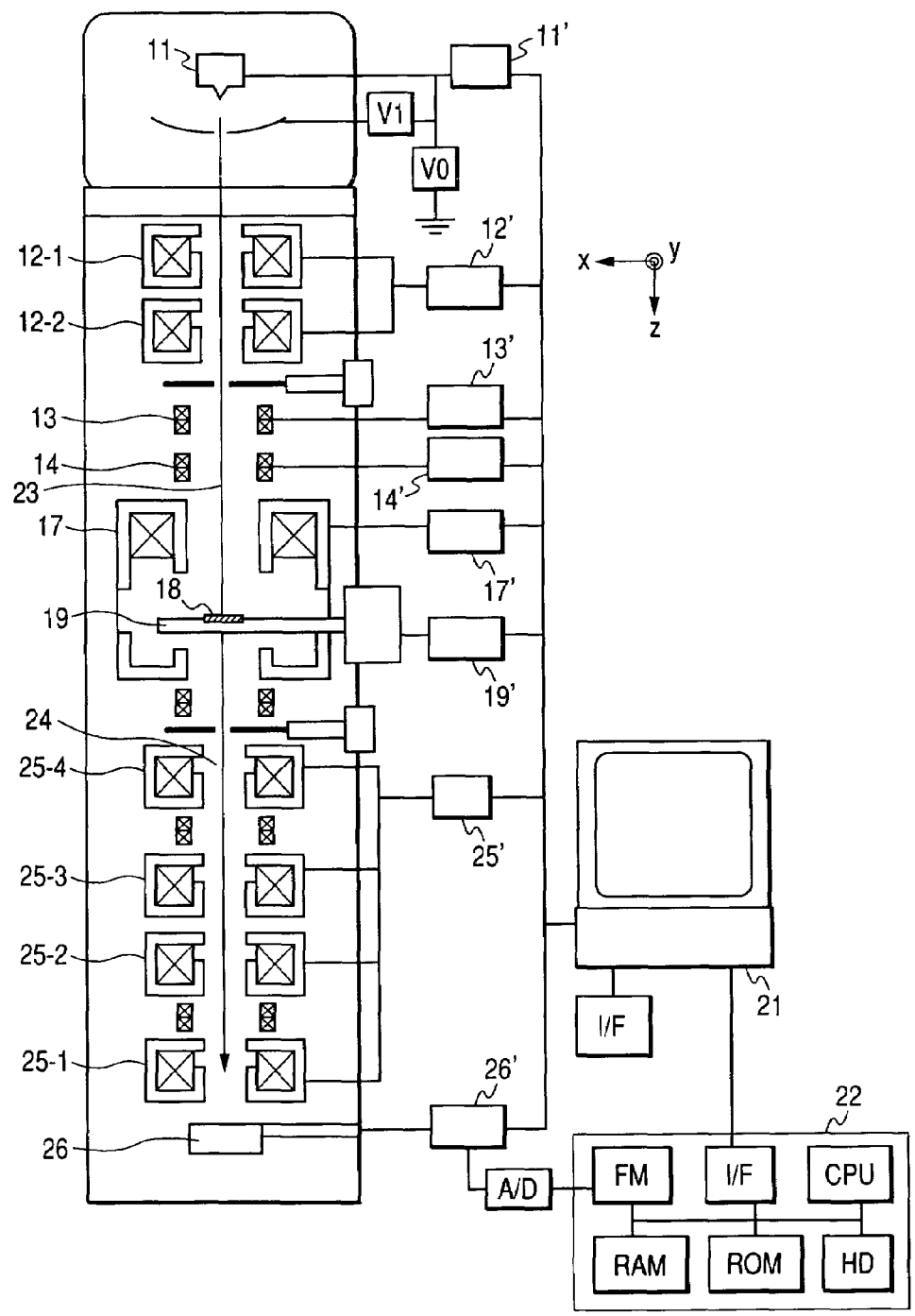
FIG. 7 is a diagram which shows the basic configuration of a TEM.

The second embodiment is directed to a method of magnification calibration in a TEM. FIG. 7 shows the diagram of a basic configuration of the TEM used in the present embodiment. This includes control unit 11' for controlling the electron gun 11, including the primary electron beam acceleration voltage and the emitting voltage. Control unit 12' controls the condenser lens 12 for adjusting the focusing condition of the primary electron beam 23 and its amperage. Control unit 13' controls the alignment deflector 13 for adjusting the incident angle of the primary electron beam 23 incident upon the specimen 19 and its amperage. Control unit 14' controls the stigmators 14 for adjusting the beam form of the primary electron beam 23 incident upon the specimen 18 and its amperage. Control unit 18' controls the objective lens 17 for adjusting the focusing position of the primary electron beam 23 to the specimen 18 and its amperage. Control unit 20' controls the specimen stage 20 for setting the position of the specimen 18 in the specimen chamber and its position. Control unit 25' controls the projective lens 25 for enlarging and projecting the transmission electron beam 24 having passed the specimen 18 and its amperage. Control unit 26' controls the electron detective camera 26 for detecting the electron beam 24 that has been enlarged and projected and its gain or offset. A computer 22 with a TEM control program, and a computer 23 with a image processing program. Each control unit is command controlled by a computer 21. Incidentally, the function of the computers 22 and 23 can be performed by a single computer.

First, the process of acquiring TEM images by using the apparatus shown in FIG. 7 will be described. The primary electron beam is emitted from the electron gun 11 at an emitting voltage V1, and an acceleration voltage VO is applied thereto. A direction nearly parallel with the optical axis of the mirror body is defined as the Z direction, and the plane nearly orthogonal with the optical axis is defined as the XY plane. A thin film forming the specimen 18 is placed on the specimen stage 20, and the primary electron beam 23 is irradiated from the Z direction. An adjustment will be made by using the condenser lens 12, the alignment deflector 13 and the stigmators 14 so that the primary electron beam 23 may be irradiated in parallel into the specimen at an incident angle parallel with the Z axis. The irradiation of a thin film specimen 18 with the primary electron beam 23 results in the penetration of most of the electrons through the specimen 18. This transmission electron beam 24 is enlarged and projected into the electron detective camera 26 by using the projective lens 25.

The magnification of TEM images for the specimen is set by the excitation current of the projective lens 25. Optical magnification is set by adjusting the excitation current of each lens, and the magnification of the whole projective lens is set. The adjustment of the magnification of TEM images for the specimen requires standard specimens that include a structure whose repetition cycle is known. However, as in the case of a TEM of the first embodiment, the magnifications at which calibration is possible by using standard specimens whose repetition cycle is known are very limited. For other magnifications, calculation values calculated by an electron optical simulator from the control current value of the projective lens 25, by taking the magnification analyzed on the standard specimens as the reference, are used. Accordingly, the displayed magnifications contain errors of approximately ±5%.

There are various factors responsible for magnification errors, including correspondence errors between the excitation current and the optical magnification in the projective lens 25, changes in the emitting condition of electrons emitted from the electron gun 11, correspondence errors between the excitation current and the optical magnification in the condenser lens 12 and the objective lens 17, and changes in the height of the specimen in the lens. The first image resulting from the analysis of magnification for the specimen by using a standard specimen, and the first apparatus conditions, such as the excitation current of each lens and the emitting voltage at that time, are recorded. The second image is taken by changing the setting of the projective lens 25, the second apparatus conditions at that time are recorded. The magnification of the second image relative to the first image is analyzed by image processing, and both the magnification of the second image relative to the specimen and the second apparatus conditions are recorded. Thereafter, magnifications in a variety of apparatus conditions are actually measured by replacing the second image, whose magnification has been analyzed by the first image, and they are recorded together with the apparatus conditions. Based on the apparatus conditions and the results of magnification analysis that have been recorded, the magnifications of the TEM are calibrated.

While in a STEM, magnification is calibrated by the control current of the scanning deflector 16, in a TEM, magnification is calibrated by changing the set conditions of the transmission lens. It is preferable to adjust the magnification calibration by means of the excitation current of the projective lens 25-1 located at the farthest position from the specimen, in other words, at the nearest position to the electron beam detective camera, among the projective lens 25. This is because, if another lens exists between the magnification adjustment lens and the electron beam detective lens, the process of adjustment will be more complicated. Only when magnification errors are important, and it has become impossible to effect adjustment only by means of the projective lens 25-1, will the excitation current of another projective lens 25 be adjusted.

Other steps will be carried out by nearly the same procedure as those employed in the magnification calibration in a STEM.

Third Embodiment

Figure 8:
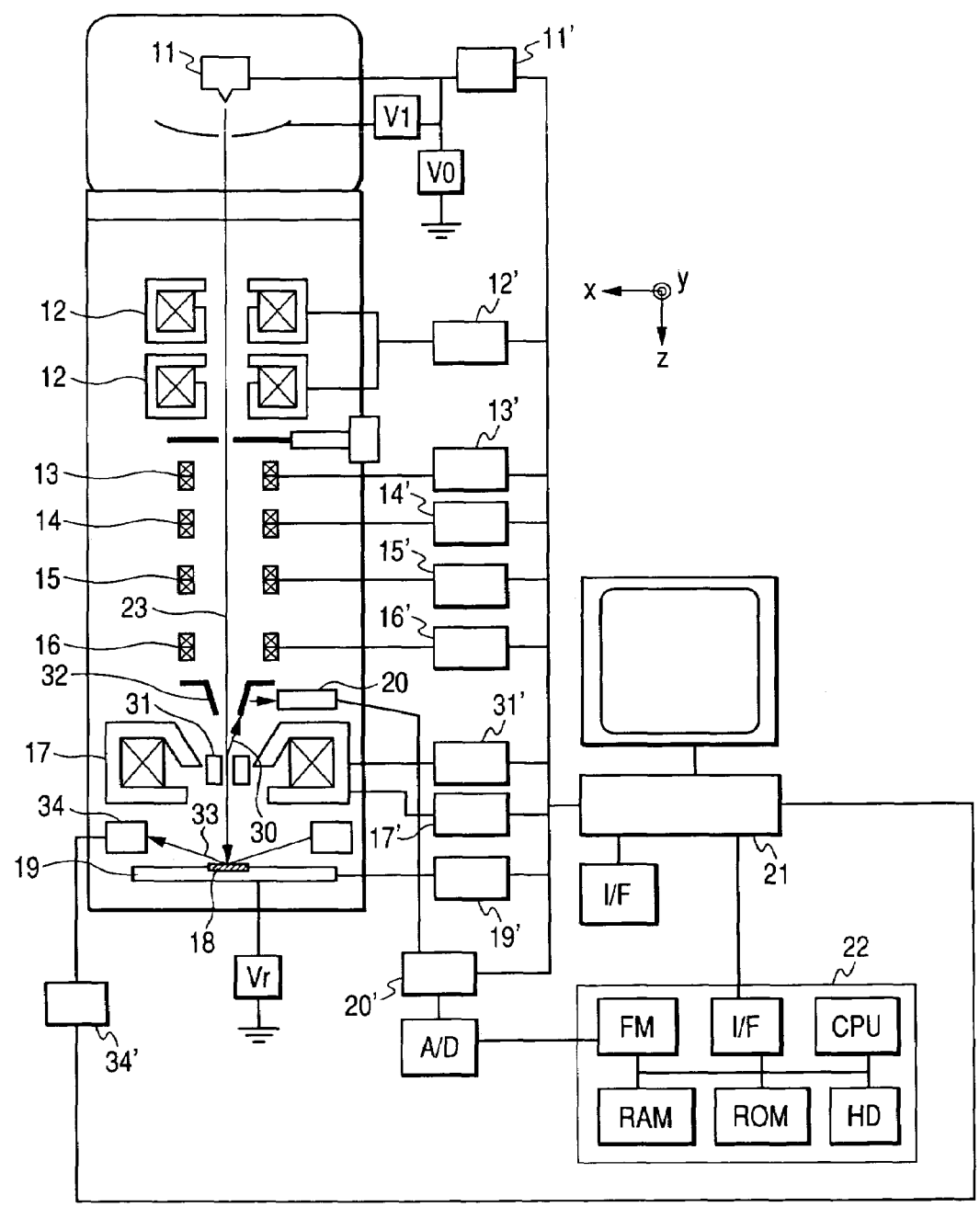
FIG. 8 is a diagram which shows the basic configuration of a SEM.

FIG. 8 is a diagram showing the basic configuration of a SEM adapted to wafer analysis according to a third embodiment. This includes a control unit 11' for controlling the electron gun 11, including the accelerating voltage and the emitting voltage of the primary electron beam. Control unit 12' controls the condenser lens 12 for adjusting the focusing condition of the primary electron beam 23 and its amperage. Control unit 13' controls the alignment deflector 13 for adjusting the incident angle of the primary electron beam 23 incident upon the specimen 18 and its amperage. Control unit 14' controls the stigmators 14 for adjusting the beam form of the primary electron beam 23 incident upon the specimen 18 and its amperage. Control unit 15' controls the image shift deflector 15 for adjusting the irradiation area of the primary electron beam 23 incident upon the specimen 18 and its amperage. Control unit 16' controls the scanning deflector 16 for raster scanning the primary electron beam 23 incident upon the specimen 18 and its amperage; a control unit 17' for controlling the objective lens 17 for adjusting the focusing position of the primary electron beam 23 to the specimen 18 and its amperage. Control unit 19' controls the specimen stage 19 for setting the position of the specimen 18 in the specimen chamber and its position. Control unit 31' controls the E×B deflector 31 for deflecting the electrons 30 emitted from the surface of the specimen and its amperage; a converter electrode 32 against which the deflected electron beam 30 collides. Control unit 20' controls the electron detective camera 20 for detecting the electron beam 23 emitted from the converter electrode and its gain or offset. The SEM also includes a specimen height sensor 34 using a laser beam 33 and a control unit 34' for controlling the same; a computer 21 with a SEM control program; and a computer 22 with an image processing program. Each control unit is command controlled by a computer 21. Optionally, the function of the computers 21 and 22 can be performed by a single computer.

The process leading to the acquisition of SEM images will now be described. The primary electron beam is emitted from the electron gun 11 by an emitting voltage V1, and an acceleration voltage V0 is applied. The direction parallel to the optical axis of the mirror body is defined as the Z direction, and the plane orthogonal to the optical axis is defined as the XY plane. The specimen 18 is inserted, the height of the specimen 18 is determined by a specimen height sensor 34 using a laser, and the focus is revised in a range in which images can be analyzed by adjusting the Z position of the specimen stage 19 or the control value of the objective lens 17, in other words, the focus is roughly adjusted. This rough adjustment may be made by confirming the image of the specimen 18 at low magnification, and by using the image. The field of view for adjusting the electron optical system is chosen by using the XY movement mechanism of the specimen stage 19. Deviation from correct alignment, focus and astigmatism are rectified in the field of view for adjusting the electron optical system. Then, the specimen stage 19 is used to move to the field of view for taking images, and, after a fine adjustment of the focus of the objective lens 19 so that the image may be observed clearly, the image is taken.

A recent SEM which is adapted for wafer measurement adopts the retarding electric field method for retarding the voltage incident upon the specimen by raising the acceleration voltage on the primary side and by applying a negative voltage on the specimen side in order to improve the space resolution (hereinafter referred to as "retarding method"). The negative voltage applied on the specimen side is called a retarding voltage Vr. In the SEM for critical dimension measurement, the retarding voltage is set in such a way that the incident voltage upon the specimen may approach zero. There is also a SEM-type testing system for testing leaks in devices by changing the electrically charged state of the specimen surface by changing the retarding voltage Vr. Any change in the retarding voltage results in a change in the magnification of the SEM image for the specimen. In a SEM adapted for wafer measurement, it is necessary to apply a retarding voltage Vr to the apparatus conditions that have been recorded together with the results of magnification analysis. As there is no assurance that the retarding voltage will be applied evenly on the whole surface of the wafer depending on the device structure formed on the wafer, it is necessary to store the position for measuring magnification in the wafer as one of the apparatus conditions.

For the analysis of the magnification of the first image for the specimen, a pattern whose repetition cycle is known among the device patterns formed on the wafer is chosen, and that repetition cycle serves as the basis for the analysis. At present, in order to minimize the errors in setting the magnification, the magnification calibrated by standard specimens and the magnification for measuring a pattern width are set almost equally. However, in order to average the pattern processing errors, it is better to take the first image at a low magnification. On the other hand, the magnification used for measuring the pattern width should be optimized by the space resolution of the SEM. And, lately, not only the pattern width, but also the unevenness of the pattern surface, are counted as items of assessment, and the necessity of observing a specimen at a further higher magnification has come out. Lowering the magnification of the first image and improving the analysis precision of the repetition cycle or the magnification precision of the first image for the specimen, taking the second image by the condition measuring pattern width, analyzing the magnification of the second image for the first image, and analyzing the magnification of the second image for the specimen contribute to the improvement of the precision of measuring and analyzing pattern dimensions.

In a STEM and a SEM, despite the differences described above, the procedure shown in FIG. 6 for recording apparatus conditions, analyzing the magnification at the time when the current amplitude of the scanning deflector is changed by the conditions mentioned above, recording the results of magnification analysis together with the apparatus conditions, and calibrating magnifications based on the results obtained, are the same.

Fourth Embodiment

The magnification analysis and calibration techniques according to the present invention are applicable not only to electron microscopes, but also to other electric charged particle beam apparatuses. The present invention is applicable, for example, to a focused ion beam (FIB) apparatus that raster scans on the specimen using a finely focused ion beam and visualizes the specimen structure by detecting the electron beam or secondary ions emitted by the specimen.

The present invention is also applicable to a variety of probe microscopes, for example scanning tunnel microscopy and atomic force microscopy.

The present invention has been described in terms of preferred embodiments. However, those skilled in the art will recognize that many variations of such embodiments exist. Such variations are intended to be within the scope of the present invention and the appended claims.

What is claimed is:

1. An electric charged particle beam microscopy wherein a specimen is irradiated with a charged particle beam, and secondary charged particles generated by the specimen are detected to thereby obtain an image of the specimen, the microscopy comprising:
a step of taking a first image with a known magnification relative to the specimen by irradiating the specimen with the charged particle beams under a first control condition;
a step of taking a second image having a common field of view with the first image by irradiating the specimen with the charged particle beam under a second control condition;
a step of image processing for analyzing a magnification of the second image relative to the first image from the common field of view;
a step of calculating the magnification of the second image relative to the specimen from the magnification of the first image relative to the specimen, and the magnification of the second image relative to the first image; and
a step of recording the magnification of the second image relative to the specimen along with the second control condition.

2. The electric charged particle beam microscopy according to claim 1, further comprising: when the magnification of the second image to the first image cannot be analyzed in the step of image processing,
a step of taking a third image having a common field of view with the first image by irradiating a specimen with electric charged particle beam under a third control condition requiring that the magnification is between magnification of the first image and magnification of the second image;
a step of image processing for analyzing the magnification of the third image relative to first image;
a step of image processing for analyzing the magnification of the second image relative to the third image; and
a step of calculating the magnification of the second image relative to the specimen from the magnification of the previous first image to the specimen, the magnification of the third image relative to the first image, and the magnification of the second image relative to the third image.

3. The electric charged particle beam microscopy according to claim 2, wherein the image processing step includes a step of calculating the Fourier transform image of an image and a step of calculating the coordinate transformed image of the Fourier transformed image, the coordinate transformed image serving as the basis of calculating magnification.

4. The electric charged particle beam microscopy according to claim 3 wherein the first control condition is a condition that enables to measure the interval between crystal lattice surfaces from the image acquired and the magnification for specimen is a magnification actually measured from the interval between lattice surfaces.

5. An electric charged particle beam application device comprising:
an electric charged particle source for generating a first electric charged particle beam;
a first electromagnetic field generator that leads the first electric charged particle beam to a specimen;
a specimen stage for setting a position of a specimen with respect to the first electric charged particle beam;
a detector for detecting secondary charged particles;
a second electromagnetic field generator that leads the secondary charged particles radiating from the specimen to the detector;
a unit for image formation for forming an image of specimen structure based on the detector output; and
a controller for setting image magnification by using the electromagnetic field generator;
wherein
the controller has a unit for magnification calibration, and the unit for magnification calibration records a first image with a known magnification relative to the specimen by irradiating the specimen with an electric charged particle beam under a first control condition, records a second image having a common field of view with the first image by irradiating the specimen with the electric charged particle beam under a second control condition, calculates a magnification of the second image relative to the first image recorded, calculates a magnification of the second image relative to the specimen from the magnification of the first image relative to the specimen and the magnification of the second image relative to the first image, and records the magnification of the second image relative to the specimen together with the second control condition.

6. The electric charged particle beam application device according to claim 5, wherein the controller sets magnification by using a deflector that constitutes the first electromagnetic field generator.

7. The electric charged particle beam application device according to claim 5, wherein the controller sets a magnification by using lens that constitute the electromagnetic field generator.

8. A critical dimension measurement method for measuring the critical dimensions of a specimen to be measured by irradiating the specimen to be measured with an electric charged particle beams, detecting electrically charged particles secondarily generated from the specimen caused by the irradiation, and inputting the image data acquired into a computer, wherein the method comprises:
a step of inputting first image data including at least a standard specimen for magnification calibration into the computer;
a step of calculating a magnification of the first image relative to the specimen by comparing an actual length of the standard specimen and a length on the first image;
a step of inputting second image data including at least a specimen to be measured for critical dimension measurement into the computer;
a step of calculating a magnification of the second image relative to the specimen by analyzing the magnification of the second image relative to the first image; and
a step of converting a length of the specimen to be measured for critical dimension measurement on the second image into an actual length.

9. A critical dimension measurement system comprising:
a specimen stage for putting a specimen to be measured and a standard specimen for calibration;

an irradiation optical system for irradiating the specimen to be measured for critical dimension measurement or the standard specimen with an electric charged particle beam;

a detector for detecting electric charged particles generated secondarily from the specimen to be measured for critical dimension measurement or the standard specimen as a result of irradiation by the electric charged particle beam;

a unit for acquiring image signals from the detector;

a magnification controller for setting a magnification of an image by an adjustment of an electron optical system;

a user interface for inputting a magnification of an image to be taken; and a critical dimension measurement unit for measuring a length of a specimen from the image signal, wherein the magnification controller sets the electron optical system at the first and second magnification conditions in response to the image magnification inputted by the user interface, and wherein the critical dimension measurement unit calculates a magnification of the first image relative to the specimen by comparing an actual length of the standard specimen and a length on a first image by using the first image of the standard specimen taken under the first magnification condition, analyzes the magnification of a second image taken under the second magnification condition relative to the first image to thereby calculate a magnification of the second image relative to the specimen, and uses the magnification information to estimate a length of the specimen to be measured for critical dimension measurement.

10. A critical dimension measurement system comprising:

a unit for image signal formation for acquiring image signals for a specimen to be measured for critical dimension measurement by irradiating the specimen with an electric charged particle beam from an electric charged particle beam source, and detecting electric charged particles generated secondarily from the specimen; and a unit for data processing for inputting image signals formed at the unit for image signal formation, processing image, and measuring a critical dimension of the specimen based on a result of the image processing; and wherein the unit for data processing calculates a magnification of a first image relative to a specimen by comparing an actual length of a standard specimen and a length in the first image based on the first image of the standard specimen taken with a magnification of under a first irradiation condition, analyzes a magnification of a second image taken under a second irradiation condition relative to the first image to thereby calculate a magnification of the second image relative to the specimen; and estimates a length of the specimen to be measured by using the magnification information.

* * * * *